United States Patent
Decoux

(10) Patent No.: US 9,240,086 B2
(45) Date of Patent: Jan. 19, 2016

(54) BANKNOTE VALIDATOR

(75) Inventor: Eric Decoux, Vevey (CH)

(73) Assignee: SICPA HOLDING SA, Prilly (CH)

( * ) Notice: Subject to any disclaimer, the term of this patent is extended or adjusted under 35 U.S.C. 154(b) by 0 days.

(21) Appl. No.: 13/504,790

(22) PCT Filed: Oct. 28, 2010

(86) PCT No.: PCT/EP2010/066381
§ 371 (c)(1),
(2), (4) Date: Apr. 27, 2012

(87) PCT Pub. No.: WO2011/051399
PCT Pub. Date: May 5, 2011

(65) Prior Publication Data
US 2012/0217416 A1     Aug. 30, 2012

Related U.S. Application Data

(60) Provisional application No. 61/255,696, filed on Oct. 28, 2009.

(51) Int. Cl.
*G01N 21/64*         (2006.01)
*G07D 7/12*          (2006.01)

(52) U.S. Cl.
CPC ............... *G07D 7/128* (2013.01); *G01N 21/64* (2013.01); *G07D 7/12* (2013.01); *G07D 7/121* (2013.01)

(58) Field of Classification Search
CPC .................................. G07D 7/12; G01N 21/64
USPC .................. 250/461.1, 556; 382/138; 356/71; 194/207
See application file for complete search history.

(56) References Cited

U.S. PATENT DOCUMENTS 5,640,463 A      6/1997  Csulits
5,806,649 A *    9/1998  Walsh et al. ................... 194/203

(Continued)

FOREIGN PATENT DOCUMENTS

AR        007379        10/1999
AR        040621         4/2005

(Continued)

OTHER PUBLICATIONS

Lynch et al., Color and Light in Nature, 2001, Cambridge University Press, 2nd Edition, p. 231—used for inherency purposes only.*

(Continued)

*Primary Examiner* — David Porta
*Assistant Examiner* — Jeremy S Valentiner
(74) *Attorney, Agent, or Firm* — Greenblum & Bernstein, P.L.C.

(57) ABSTRACT

The present invention relates to the technical field of devices for reading/authenticating banknotes. The invention also concerns handheld devices, particularly those which may be used by visually impaired persons, to identify different banknote denominations. The present invention is aimed at providing a banknote validator that avoids the drawbacks of the prior art. The validator according to the invention may as well be used for validating a security document including a marking (like luminescent ink or pattern printed on said document, luminescent security thread or strip, for example) operable to glow with a specific color luminescence under appropriate UV light illumination. The invention further describes a method for identifying a denomination of a banknote having a test zone including a marking operable to glow with a specific color luminescence according to the denomination under appropriate UV light illumination.

4 Claims, 11 Drawing Sheets

(56) References Cited

U.S. PATENT DOCUMENTS

| | | | |
|---|---|---|---|
| 5,915,518 A * | 6/1999 | Hopwood et al. | 194/207 |
| 5,960,103 A | 9/1999 | Graves et al. | |
| 5,966,456 A | 10/1999 | Jones et al. | |
| 6,223,876 B1 | 5/2001 | Walsh et al. | |
| 7,378,665 B2 | 5/2008 | Schuett et al. | |
| 7,550,736 B2 | 6/2009 | Schuett et al. | |
| 2004/0031931 A1 | 2/2004 | Muller et al. | |
| 2004/0145726 A1 | 7/2004 | Csulits et al. | |
| 2004/0240722 A1 * | 12/2004 | Tsuji et al. | 382/137 |
| 2005/0236481 A1 * | 10/2005 | Gascoyne et al. | 235/454 |
| 2005/0257270 A1 | 11/2005 | Grassl et al. | |
| 2007/0210574 A1 * | 9/2007 | Schwenk et al. | 283/92 |

FOREIGN PATENT DOCUMENTS

| | | |
|---|---|---|
| CN | 2187815 | 1/1995 |
| CN | 2496076 | 6/2002 |
| CN | 1429379 | 7/2003 |
| CN | 201270548 | 7/2009 |
| EP | 1 576 549 | 6/2007 |
| EP | 1 471 472 | 6/2009 |
| GB | 2 355 522 | 4/2001 |
| KR | 100813144 | 3/2008 |
| TW | M265723 | 5/2005 |

OTHER PUBLICATIONS

Partial English language translation of Argentina Office action conducted in counterpart Argentina Appln. No. 20100103899 (Mar. 17, 2013).

English translation of Taiwan Office Action/Search Report conducted in counterpart Taiwan Appln. No. 99136412 (Oct. 21, 2013).

Partial English language translation of Singapore Office action conducted in counterpart Singapore Appln. No. 201202960-9 (Jul. 17, 2013).

Chinese Office Action conducted in counterpart Chinese Appln. No. 201080049807.4 (Apr. 21, 2014) w/ English language translation.

* cited by examiner

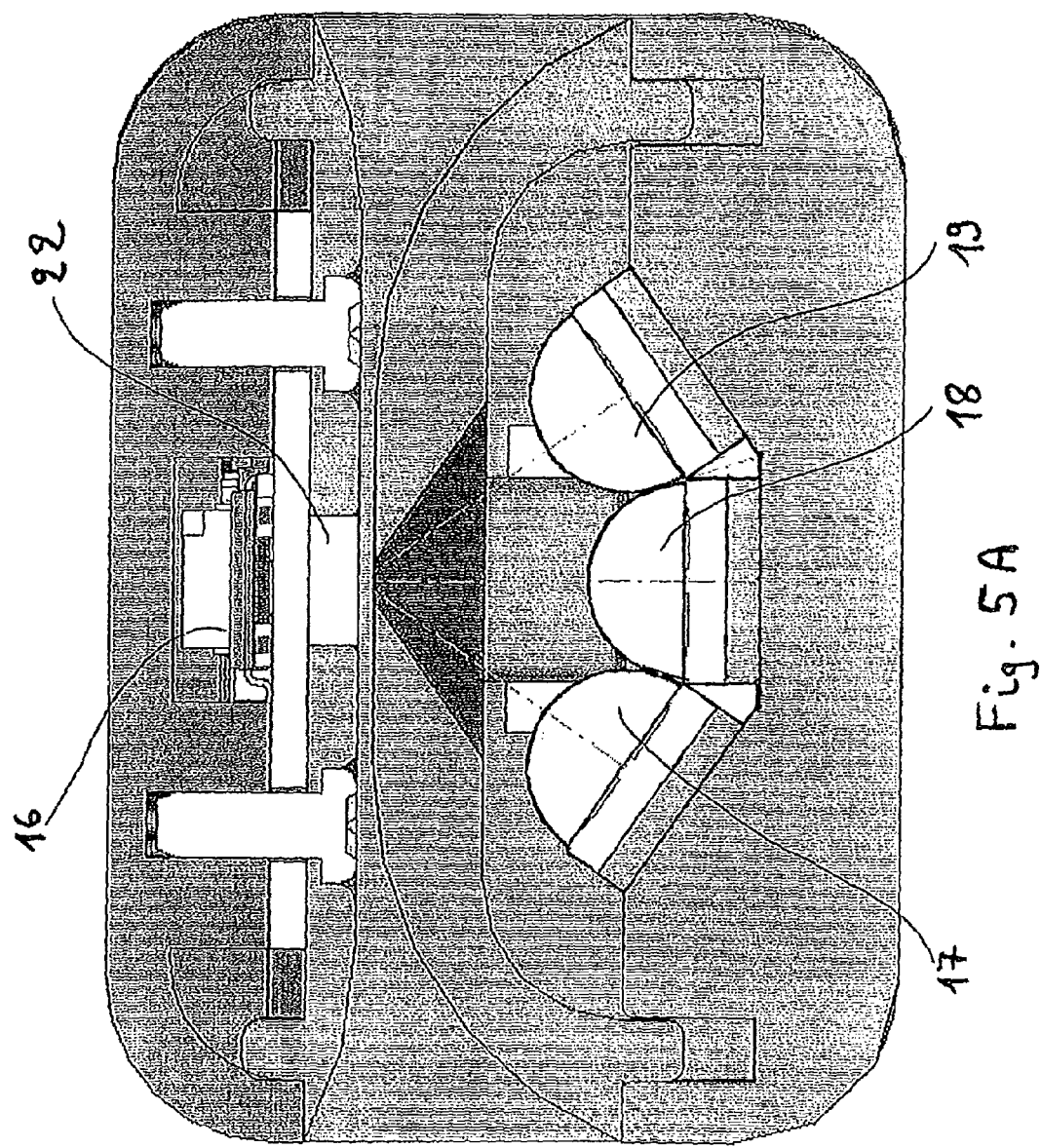

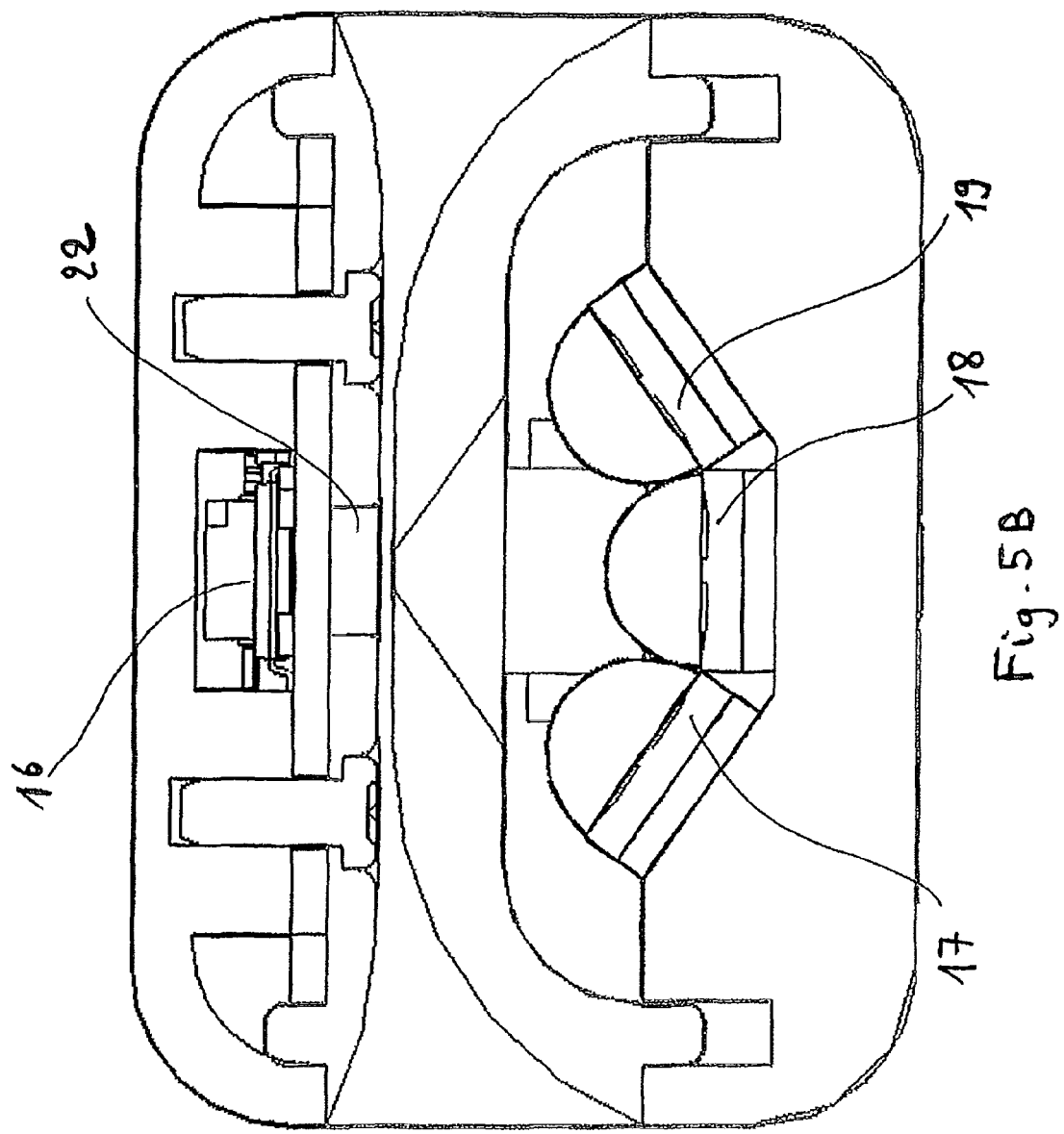

BANKNOTE VALIDATOR

CROSS-REFERENCE TO RELATED APPLICATIONS

The present application is a U.S. National Stage of International Patent Application No. PCT/EP2010/066381 filed Oct. 28, 2010 and claims the benefit of U.S. Provisional Application No. 61/255,696 filed Oct. 28, 2009.

BACKGROUND OF THE INVENTION

1. Technical Field

The present invention relates to the technical field of devices for reading/authenticating banknotes. The invention also concerns handheld devices, particularly those which may be used by visually impaired persons, to identify different banknote denominations.

2. Discussion of Background Information

Optical properties of specific marking on currencies, or of the paper itself, are often used for discouraging forgery. For example, it is well known that high-quality non-fluorescent paper (not commonly available to the general public) is used for many currencies. This feature allows simply detecting forgery obtained by photocopying a banknote using conventional photocopier paper, as said paper fluoresces under UV light illumination due to the presence of optical brightner agent (which absorbs UV light to emit light at a higher wavelength in the visible region). Many other types of marking are known in the art: for example, luminescent ink or pattern printed on the banknote, a strip or a (possibly luminescent) security thread, marking with IR absorbing ink etc.

Other illustrative and non-limiting examples are the Canadian currency, which includes random points having bright secondary emission when exposed to UV light, or the Peruvian currency, which too has specific small features having bright secondary emission when exposed to UV light.

Banknote validators are of common use for scanning a banknote and determining its denomination and/or authenticating it, as illustrated, for example, with the banknote validators disclosed in the following U.S. Pat. No. 5,640,463, U.S. Pat. No. 5,960,103, U.S. Pat. No. 7,378,665 B2, U.S. Pat. No. 7,550,736 B2 and EP 1 471 472 B1, or the patent application GB 2 355 522 A.

Typically, these banknote validators use reflectance and/or transmittance properties of the banknotes relating to certain currencies, under illumination by appropriate light (for example, UV, white or IR light), to determine a denomination or check authenticity by comparing intensities, intensity thresholds, or intensity ratios, of light reflected and/or transmitted by said banknotes with some corresponding reference values for authentic banknotes.

Some banknotes validators can further detect the presence of fluorescent and/or phosphorescent material (i.e. luminescent material) on or within the banknotes, or even measure the corresponding luminescence intensity.

However, using reflectance or transmittance intensities, or luminescence intensity, necessitates having separate intense pulsed light sources (such as high-intensity emitting diodes), and adapted lenses to focalize reflected/transmitted light and obtain measurement data with a good signal/noise ratio. This makes miniaturization of the scanning head of a validator more difficult and increases its cost, particularly in case of a handheld validator. Moreover, using mere reflectance or transmittance intensities, cannot always allow discriminating certain denominations or discriminating counterfeit banknote. For example, for genuine US currency reflecting a high level of UV light without overall fluorescence, it is not possible to discriminate a counterfeit currency having these characteristics.

Some banknote validators, for better discriminating various denominations, use imaging of a specific marking of a banknote, or detection of marking with magnetic ink or conductivity properties, at a given place on the banknote (for example, a specific pattern printed on the banknote, a strip or a security thread, or a portion free of printed matter). However, as the position of the marking generally changes between denominations and series, these validators necessitates using a further means for distinguishing width from length and transporting the banknotes along a path through a banknote passageway, which includes control means and sensors for measuring a position of the banknote in said passageway during a scanning operation, so as to correctly find and detect properties of the marking. This is even more complex in case said checking must be performed whatever is an insertion sense and/or side of the banknote in the passageway. Besides being detrimental to miniaturization of the scanning head of the validator, this further means for transporting the banknote is not appropriate for a handheld equipment to be used by users (like visually impaired persons, for example). Indeed, said users would prefer inserting the banknote and simply passing it through the validator for scanning operation, while still holding the banknote.

Thus, there is clearly a need for a robust banknote validator capable to fully discriminate the denominations of a currency and reliably authenticate these denominations, which could even be a handheld device. Particularly, there is a need for such an handheld banknote validator adapted to visually impaired persons, as it is clear from a recently published report of ARINC Engineering services, LLC, for the Bureau of Engraving and Printing (BEP), which is a bureau within the United States Department of Treasury (Final Report, "Study to Address Options for Enabling the Blind and Visually Impaired Community to Denominate US Currency, contract S08-00156, July 2009).

SUMMARY OF THE INVENTION

The present invention is aimed at providing a banknote validator that avoids the above mentioned drawbacks of the prior art. The validator according to the invention may as well be used for validating a security document including a marking (like luminescent ink or pattern printed on said document, luminescent security thread or strip, for example) operable to glow with a specific color luminescence under appropriate UV light illumination.

According to one aspect of the invention, a banknote validator for identifying a denomination of a banknote having a test zone including a marking operable to glow with a specific color luminescence according to the denomination under appropriate UV light illumination, comprises:

a housing provided with a banknote passageway;

a first UV light source operable to irradiate one side of the test zone of the banknote in the passageway with UV light in first wavelength range, and a first color sensor operable to receive corresponding first excited luminescence light transmitted through, or reflected from, said test zone;

a second UV light source operable to irradiate one side of the test zone of the banknote with UV light in a second wavelength range, distinct of said first wavelength range, and a second color sensor operable to receive corresponding second excited luminescence light transmitted through, or reflected from, said test zone;

a communicator operable to indicate a denomination of the banknote; and a processor operable to control the first and second UV light sources, the first and second color sensors and the communicator, and comprising a memory, wherein, said processor is further operable to:

determine a first color value of the first excited luminescence light from a first signal received from the first color sensor;

determine a second color value of the second excited luminescence light from a second signal received from the second color sensor;

compare said determined color values with stored distinct reference color values corresponding to distinct denominations, respectively for luminescence under UV light in said first and second wavelength ranges and, in case the determined color values match reference color values, determine that the denomination of the banknote corresponds to that associated with said reference color values; and control the communicator to indicate the determined denomination.

By contrast with the above mentioned prior art, the banknote validator according to the invention uses color sensors, i.e. not mere fluorescence sensors for measuring only fluorescent light intensities, but photodiodes equipped with filters (for receiving a luminescence light only within a wavelength window) which allow determining both a mean wavelength and an amplitude of the detected excited luminescent light. Indeed, this is the chromatic part of the signal, which is a function of the wavelength of the excitation light, that is used for determining a color value (corresponding to said mean wavelength and amplitude) of the excited luminescent light. A color sensor is not necessarily an expensive component like a spectrophotometer, but may be a simple economical RGB photodiode, for example.

The use of measured luminescence color values, for comparison with reference color values corresponding to genuine distinct denominations, allows more precisely and finely characterizing the various denominations of a given currency and also constitutes an authentication test. Using such color sensors thus clearly improves reliability of the determination/authentication of a banknote denomination, over more conventional reflectance and/or transmittance measurements or fluorescence intensity measurements. Also, using at least two UV excitation light sources, emitting within two different excitation wavelength windows, and thus obtaining two luminescence color values, allows further improving discrimination of the various currency denominations.

Moreover, once the banknote validator is switched on and illumination of the banknote passed in the passageway is performed, a luminescence signal is detected by a color sensor (thanks to the wavelength filters blocking light wavelengths outside the wavelength window of the sensor) as soon as the luminescent marking on the banknote crosses said sensor, and a corresponding luminescence color value is then determined in a very short time (typically about 1 to 10 ms). Consequently, there is no need for the transport means and means for determining a position of the marking in the passageway in the above-described known art: determination of a color value is directly triggered by the detection of a luminescence signal. This makes the validator cheaper and easier to miniaturize.

In an embodiment of the above banknote validator according to the invention, the communicator is further operable to indicate that the banknote is not identified; and, in case the processor judges that a determined color value does not match any of the stored reference color values, said processor is further operable to control the communicator to indicate that the banknote denomination is not identified.

A presence of a decay under appropriate UV illumination (due to phosphorescent material in the marking) is a security feature difficult to counterfeit, and constitutes a further discrimination test.

Accordingly, the processor of the banknote validator of the invention may be further operable to:

control said first UV light source and first color sensor, or said second UV light source and said second color sensor, so as to illuminate the banknote, interrupt said illumination of the banknote and detect a decay of the corresponding excited luminescence light; and control the communicator to indicate the denomination only if said denomination is further compatible with the detected decay.

Improved discrimination and/or authentication is obtained if a decay time value (depending on denomination) is measured and compared to reference values relating to genuine denominations, in case of a presence of a decay under appropriate UV illumination. Accordingly, the processor of above mentioned banknote validator may be further operable to:

control said first UV light source and first color sensor, or said second UV light source and said second color sensor, so as to illuminate the banknote, interrupt said illumination of the banknote and measure a decay time value of the excited luminescence light;

compare the measured decay time value with stored distinct reference decay time values corresponding to distinct denominations; and in case the determined color values match reference color values, determine that the denomination of the banknote corresponds to that associated with said reference color values only if said measured decay time value further matches a reference decay time value corresponding to said denomination.

In order to detect forgeries relating to use of paper containing an optical brightener agent, which will reveal a dominant blue color all along the banknote under UV illumination, the banknote validator according to the invention may have said processor further operable to:

control the first light source and the first color sensor, or the second light source and the second color sensor, so as to detect a presence of a dominant blue color, based on color values determined from signals received from the first or second color sensor corresponding to light emitted from a plurality of parts of the test zone having passed in the passageway; and in case a presence of a dominant blue color is detected, control the communicator to indicate that the banknote is not valid.

Moreover, forgeries based on a use of highlighter pen inks are frequent and must be detected. These highlighter pen inks have the property to fluoresce under blue light illumination.

Accordingly, the above banknote validator may further comprise:

a third light source operable to irradiate one side of the test zone of the banknote in the passageway with a third light having a blue light component, and a third color sensor operable to receive corresponding third excited luminescence light transmitted through, or reflected from, the test zone;

wherein said processor is further operable to:

control the third light source and the third color sensor so as to detect a presence of a corresponding luminescence color, based on test zone luminescence color values determined from signals received from the third color sensor corresponding to light emitted from a plurality of parts of the test zone having passed in the passageway in response to the third light illumination; and in case a presence of said corresponding luminescence color is detected, control the communicator to indicate the banknote is not valid.

Said third light source may be, for example, a white light source. It is indeed just necessary that the emitted third light includes a substantially blue light component.

Preferably, in the banknote validator of the invention, depending on the embodiment, at least one of the first, second and third light source may be a Light-Emitting-Diode (LED). This makes easier miniaturization of the validator. Moreover, LEDs directly equipped with a lens for focusing emitted light on a spot are now available.

Preferably, at least one of the color sensors may be a RGB photodiode, or, depending on the embodiment, one same RGB photodiode may serve as both the first, second and third color sensors. This configuration lowers the cost and consumption of the validator, and also allows reducing dimensions of the validator.

The banknote validator according to the invention, in any of the above mentioned embodiments, may further have the passageway arranged to allow the banknote to be moved along a scanning direction corresponding to a length or a width of the banknote; two of the light sources, and the corresponding color sensors, being distinct and aligned in a direction approximately transverse to (or not aligned with) said scanning direction; and the processor is further operable to control said two light sources and the corresponding color sensors, so as to determine a color profile along said scanning direction relating to each of said light sources and compare said determined color profiles with stored distinct reference color profiles corresponding to distinct denominations and, in case the determined color profiles match reference color profiles, determine that the denomination of the banknote corresponds to that associated with said reference color profiles.

In the above configuration, the banknote validator allows determining at least two color profiles all along the length, or width, of the banknote as it is moved in the passageway. It is thus possible to determine up to three color profiles, in case the validator includes the above mentioned third light source and third color sensor, and the three light sources are not aligned in said scanning direction, as well as the corresponding three color sensors (for example, they may form a linear array of sources, and a corresponding linear array of sensors, in a transverse direction with respect to the scanning direction). The comparison of these measured color profiles with reference color profiles of genuine denominations makes the determination and/or authentication of a denomination more reliable, particularly in case these color profiles are transmission color profiles. Further, in case the third light source is a white light source and the third color sensor is a RGB photodiode, the corresponding color profile is richer and thus, even more discriminating (as the measured RGB color profile is three dimensional).

Due to the possibilities of miniaturization offered by the validator according to the invention, any of the above mentioned embodiments may correspond to a handheld banknote validator.

Another aspect of the invention relates to a method for identifying a denomination of a banknote as indicated in the appended claims, and corresponding to the embodiments of the banknote validator as described above.

Particularly, the invention also relates to a method for identifying a denomination of a banknote having a test zone including a marking operable to glow with a specific color luminescence according to the denomination under appropriate UV light illumination, comprising the steps of:

irradiating one side of the test zone of the banknote with UV light in first wavelength range by a first UV light source, and determining a first color value of a corresponding first excited luminescence light by a first signal from a first color sensor operable to receive said first excited luminescence light transmitted through, or reflected from, said test zone;

irradiating one side of the test zone of the banknote with UV light in a second wavelength range, distinct of said first wavelength range, by a second UV light source, and determining a second color value of a corresponding second excited luminescence light by a second signal from of a second color sensor operable to receive said second excited luminescence light transmitted through, or reflected from, said test zone;

comparing, via a control unit including a processor, said determined color values with given distinct reference color values corresponding to distinct denominations, stored in a memory of said processor, respectively for luminescence under UV light in said first and second wavelength ranges and, in case the determined color values match reference color values, determining that the denomination of the banknote corresponds to that associated with said reference color values; and controlling a communicator to indicate the determined denomination.

Embodiments of the invention are directed to a banknote validator for identifying a denomination of a banknote having a test zone including a marking operable to glow with a specific color luminescence according to the denomination under appropriate UV light illumination. The banknote validator includes a housing provided with a banknote passageway, a first UV light source structured and arranged to irradiate in the passageway the test zone of the banknote with UV light in a first wavelength range to create a first excited luminescence light at least one of transmitted through and reflected from the test zone, a first color sensor structured and arranged to receive the first excited luminescence light, a second UV light source structured and arranged to irradiate the test zone of the banknote with UV light in a second wavelength range, distinct from the first wavelength range, to create a second excited luminescence light at least one of transmitted through and reflected from the test zone, and a second color sensor structured and arranged to receive corresponding second excited luminescence light. Further, a communicator is structured and arranged indicate a denomination of the banknote, and a processor is configured to control the first and second UV light sources, the first and second color sensors and the communicator. The processor includes a memory, and the processor is further configured to determine a first color value of the first excited luminescence light from a first signal received from the first color sensor; determine a second color value of the second excited luminescence light from a second signal received from the second color sensor; compare the first and second color values with respective stored reference color values associated with luminescence under UV light in one of the first and second wavelength ranges; determine a denomination of the banknote from reference color values corresponding to the first and second color values; and control the communicator to indicate the determined denomination.

According to embodiments of the instant invention, the first UV light source can be structured and arranged to irradiate in the passageway one side of the test zone of the banknote in the passageway with UV light in the first wavelength range, and the second UV light source may be structured and arranged to irradiate one side of the test zone of the banknote in the passageway with UV light in the second wavelength range.

In accordance with other embodiments, the reference color values corresponding to the first and second color values may be distinct for each denomination.

Further, when at least one of the first and second color values does not match any of the stored reference color values, the processor can further be configured to control the communicator to indicate that the banknote denomination is not identifiable.

According to other embodiments of the invention, the processor can be further configured to control one of the first UV light source and the first color sensor or the second UV light source and the second color sensor so as to illuminate the banknote, interrupt the illumination of the banknote and detect a decay of a corresponding excited luminescence light and to control the communicator to indicate the denomination only when the detected decay corresponds with the denomination.

In accordance with still other embodiments, the processor may be further configured to control one of the first UV light source and the first color sensor or the second UV light source and the second color sensor to illuminate the banknote, interrupt the illumination of the banknote and measure a decay time value of the excited luminescence light, to compare the measured decay time value with stored distinct reference decay time values corresponding to distinct denominations, and when the determined color values match reference color values for a particular denomination, to determine that the measured decay time value matches a reference decay time value corresponding to the particular denomination.

Moreover, the processor can be further configured to control one of the first light source and the first color sensor or the second light source and the second color sensor to detect a presence of a dominant blue color, based on color values determined from signals received from the one of the first or second color sensor corresponding to light emitted from a plurality of parts of the test zone having passed in the passageway, and when a presence of a dominant blue color is detected, control the communicator to indicate that the banknote is not valid.

According to still further embodiments, the banknote validator can also include a third light source structured and arranged to irradiate in the passageway the test zone of the banknote with a third light having a blue light component to create a third excited luminescence light at least one of transmitted through and reflected from the test zone, and a third color sensor structured and arranged to receive corresponding third excited luminescence light. The processor can be further configured to control the third light source and the third color sensor to detect a presence of a corresponding luminescence color, based on test zone luminescence color values determined from signals received from the third color sensor corresponding to light emitted from a plurality of parts of the test zone having passed in the passageway in response to the third light illumination, and when a presence of the corresponding luminescence color is detected, control the communicator to indicate the banknote is not valid.

In embodiments, at least one of the first and second light sources can include an LED.

According to still other embodiments, at least one of the color sensors may include an RGB photodiode.

In accordance with further embodiments of the invention, the first and second color sensors may be arranged in a same RGB photodiode. Further, the first, second and third color sensors can be arranged in a same RGB photodiode.

In still further embodiments, the passageway can be structured to allow the banknote to be moved in a scanning direction corresponding to a least one of a length and a width of the banknote. The first and second light sources and the corresponding first and second color sensors may be distinct from one another and can be aligned in a direction approximately transverse to the scanning direction. Further, the processor can be further configured to control the first and second two light sources and the corresponding first and second color sensors to determine a color profile along the scanning direction relating to each of the first and second light sources, to compare the determined color profiles with stored distinct reference color profiles corresponding to distinct denominations, and when the determined color profiles match reference color profiles, to determine that the denomination of the banknote corresponds to a denomination associated with the reference color profiles.

According to still other embodiments of the invention, the banknote validator can be a hand-held device.

Embodiments of the invention are directed to a method for identifying a denomination of a banknote having a test zone including a marking operable to glow with a specific color luminescence according to the denomination under appropriate UV light illumination. The method includes irradiating the test zone of the banknote with UV light in a first wavelength range to generate a first excited luminescence light at least one of transmitted through or reflected by the test zone, determining a first color value of a received first excited luminescence light, irradiating the test zone of the banknote with UV light in a second wavelength range to generate a second excited luminescence light at least one of transmitted through, or reflected from the test zone, and determining a second color value of the second excited luminescence light. The method also includes comparing the determined color values with respective distinct reference color values for luminescence under UV light in the first and second wavelength ranges, respectively, determining a denomination of the banknote based upon reference color values corresponding to the first and second color values; and communicating the determined denomination.

According to embodiments, when a determined color value does not match any of the stored reference color values, the method can further include communicating that the banknote denomination is not identified.

In accordance with other embodiments of the instant invention, the method can further include controlling at least one of the first UV light source and the first color sensor, or the second UV light source and the second color sensor to illuminate the banknote, to interrupt the illumination of the banknote and to detect a decay of a corresponding excited luminescence light, and communicating the denomination only when the detected decay corresponds with a decay associated with the denomination.

Further, the method may include controlling at least one of the first UV light source and the first color sensor or the second UV light source and the second color sensor to illuminate the banknote, to interrupt the illumination of the banknote and to measure a decay time value of the excited luminescence light, comparing the measured decay time value with stored distinct reference decay time values corresponding to distinct denominations, and when the determined color values match reference color values, determining that the denomination of the banknote corresponds to a denomination value associated with the reference color values when the measured decay time value matches a reference decay time value corresponding to the denomination value.

In accordance with still other embodiments, the method may include controlling at least one of the first light source and the first color sensor or the second light source and the second color sensor to detect a presence of a dominant blue color, based on color values determined from signals received from the at least one of the first or second color sensor corresponding to light emitted from a plurality of parts of the test zone, and when a presence of the dominant blue color is detected, communicating that the banknote is not valid.

According to further embodiments, the method can include controlling a third light source to irradiate the test zone of the banknote with a third light having a blue light component, to generate a third excited luminescence light at least one of transmitted through and reflected from the test zone, detecting a presence of a corresponding luminescence color, based on test zone luminescence color values determined from signals received corresponding to light emitted from a plurality of parts of the test zone in response to the third light illumination, and when the corresponding luminescence color is detected, communicating that the banknote is not valid.

In further embodiments, a passageway can be structured to pass the banknote in a scanning direction corresponding to a length or a width of the banknote, and two light sources and respective color sensors are aligned approximately transverse to the scanning direction, so that the method may further include controlling the two light sources and the respective color sensors to determine a color profile along the scanning direction relating to each of the light sources, comparing the determined color profiles with stored distinct reference color profiles corresponding to distinct denominations, and when the determined color profiles match reference color profiles, determining the denomination of the banknote corresponds to that associated with the reference color profiles.

In accordance with still yet other embodiments of the present invention, a first light source can be arranged to irradiate with UV light in the first wavelength range and a first color sensor may be arranged to determine the first color value, and a second light source can be arranged to irradiate with UV light in the second wavelength range and a second color sensor may be arranged to determine a second color value of the second excited luminescence light.

The present invention will be described more fully hereinafter with reference to the accompanying drawings in which like numerals represent like elements throughout the different figures, and in which prominent aspects and features of the invention are illustrated.

BRIEF DESCRIPTION OF THE DRAWINGS

FIGS. 5A-5B illustrate sectional views of the light sources and color sensors of the banknote validator of FIGS. 1-4.

DETAILED DESCRIPTION

Figure 1:
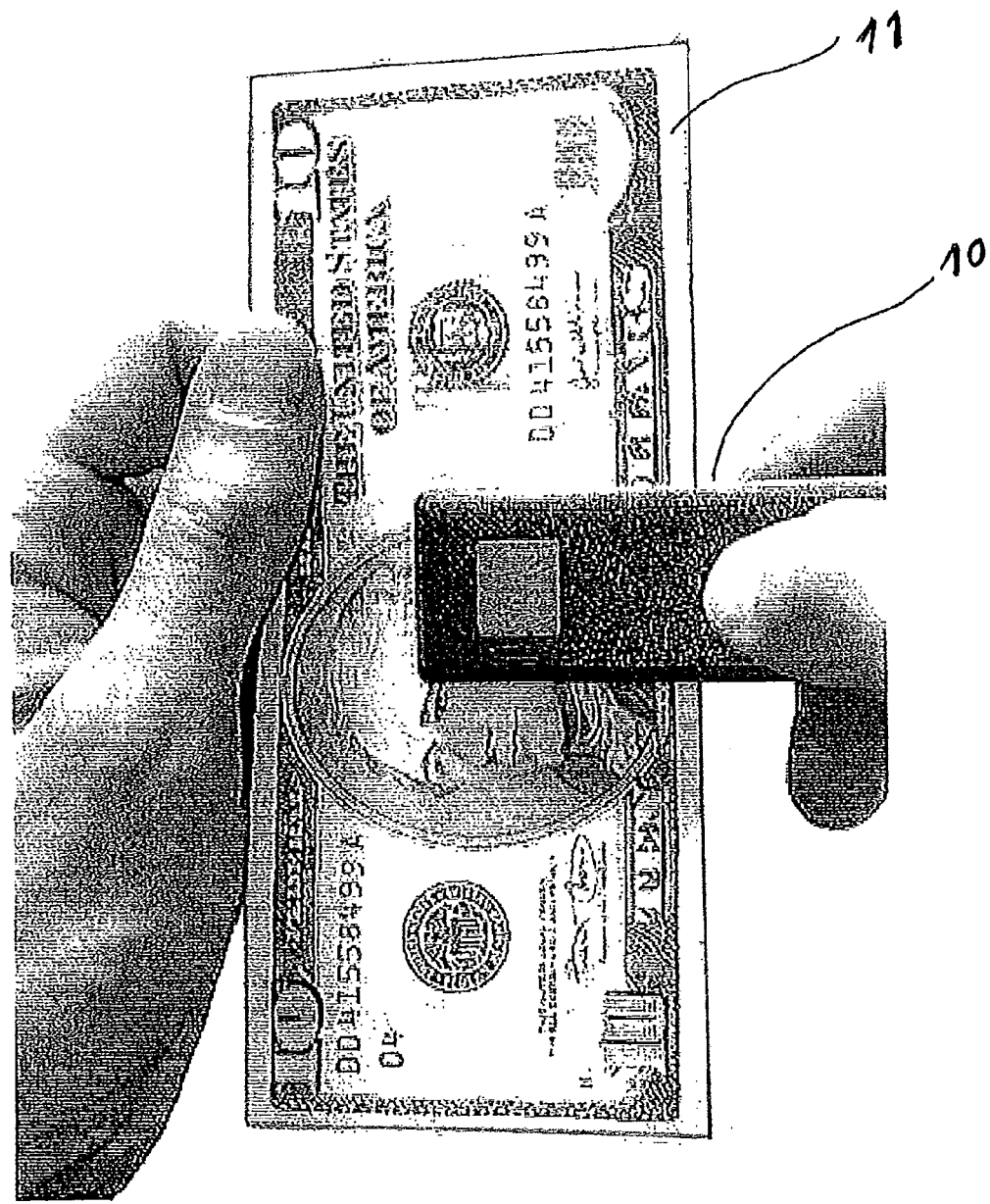
FIG. 1 illustrates a top view of a handheld banknote validator according to the invention.

An embodiment of a banknote validator according to the invention is illustrated in FIG. 1 showing a top view of a handheld banknote validator hold by a user, wherein a $10 denomination of the US currency is inserted by the user in a banknote passageway having the form of a clip (U-shaped). The invention is however not limited to handheld devices.

In the following detailed description, we use the US currency for illustrative purpose only. Such currency is one example of those currencies having a test zone including a marking (here a luminescent security thread, disposed at different positions according to the banknote denomination) operable to glow with a specific color luminescence according to the denomination under appropriate UV light illumination. Indeed, US currency, in addition to an overall minimal response to UV light exposure, has security threads (markings) for individual denominations which emit light due to secondary emissions at different wavelength under appropriate UV light exposure. These security threads have the following characteristic fluorescence colors, depending on the denomination (this feature, implemented in the 1996 series for the first time, is present on most circulating banknotes), when exposed to appropriate UV light:
 blue for the 5 dollars denomination;
 orange for the 10 dollars denomination;
 green for the 20 dollars denomination;
 yellow for the 50 dollars denomination; and
 red for the 100 dollars denomination.

Moreover, the security threads in the $100 and $10 new series have further characteristic decay properties under UV light exposure.

However, other currencies having specific luminescent markings, may have been considered for the invention (of course, the light sources, and corresponding color sensors, must be adapted to the specific wavelength values for revealing said marking).

In the following illustrative detailed embodiment of the banknote validator according to the invention, LEDs are used as light sources and RGB photodiodes are used as color sensors. Moreover, for compactness reasons, the color sensors are configured for detecting light transmitted through the banknote in the passageway. However, configurations of the light sources and color sensors for detection in reflection only, or in reflection and transmission (depending on the coupled light source and corresponding color sensor considered), are also possible (as is well known to the skilled person) but are not represented here.

Figure 2A:
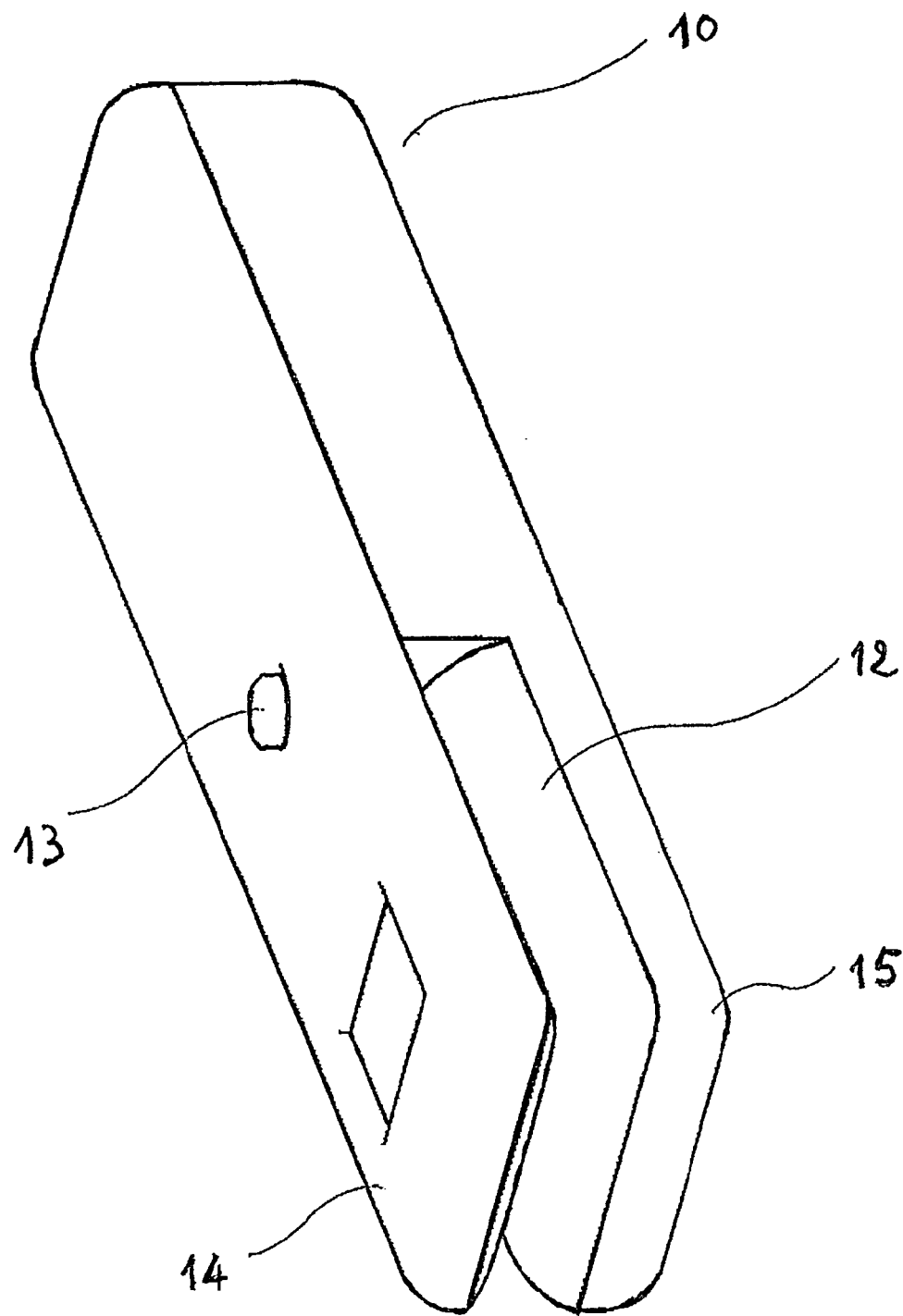
FIG. 2A illustrates a perspective view of a handheld banknote validator according to the invention.
Figure 2B:
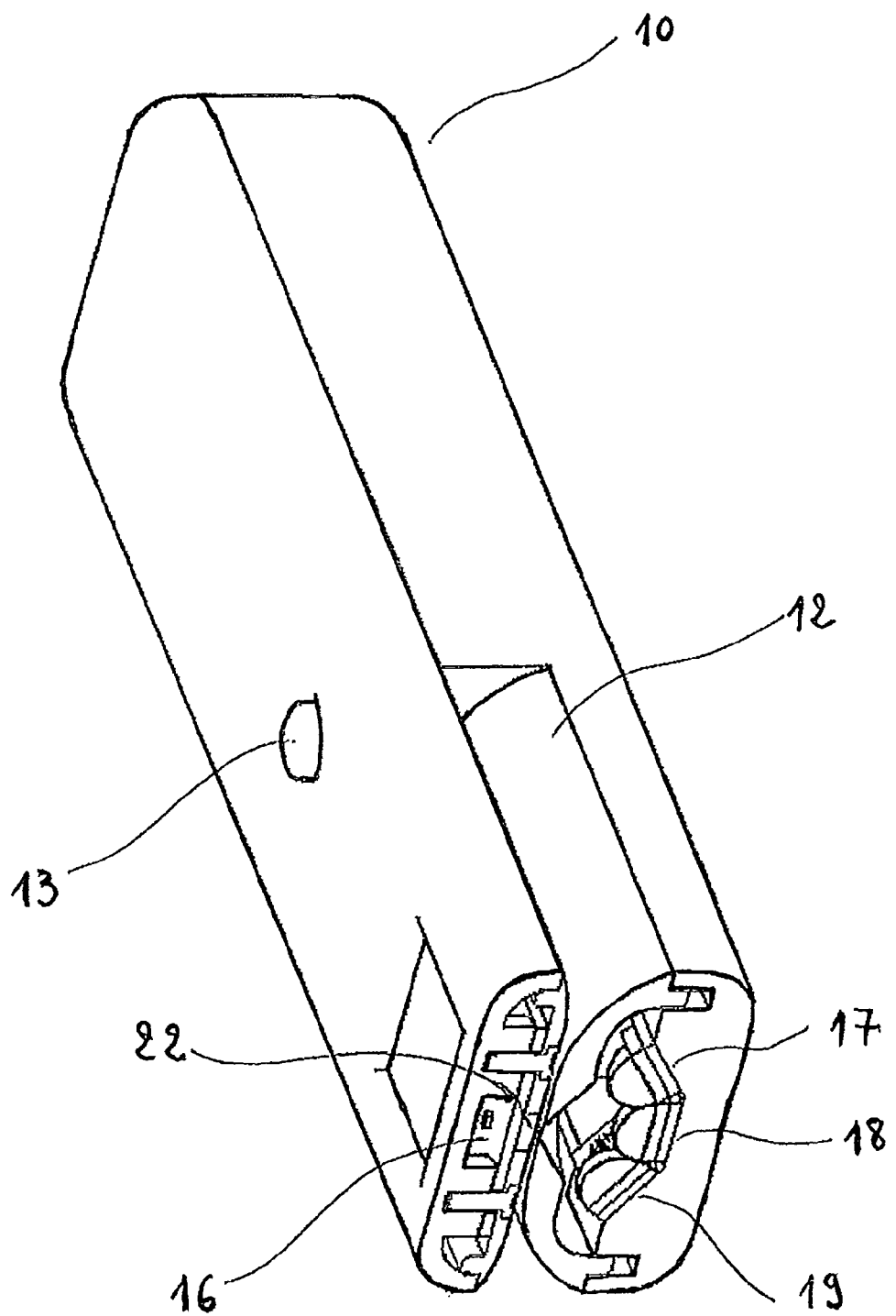
FIG. 2B illustrates a partially cut-away perspective view of the handheld banknote validator of FIG. 1.
Figure 3A:
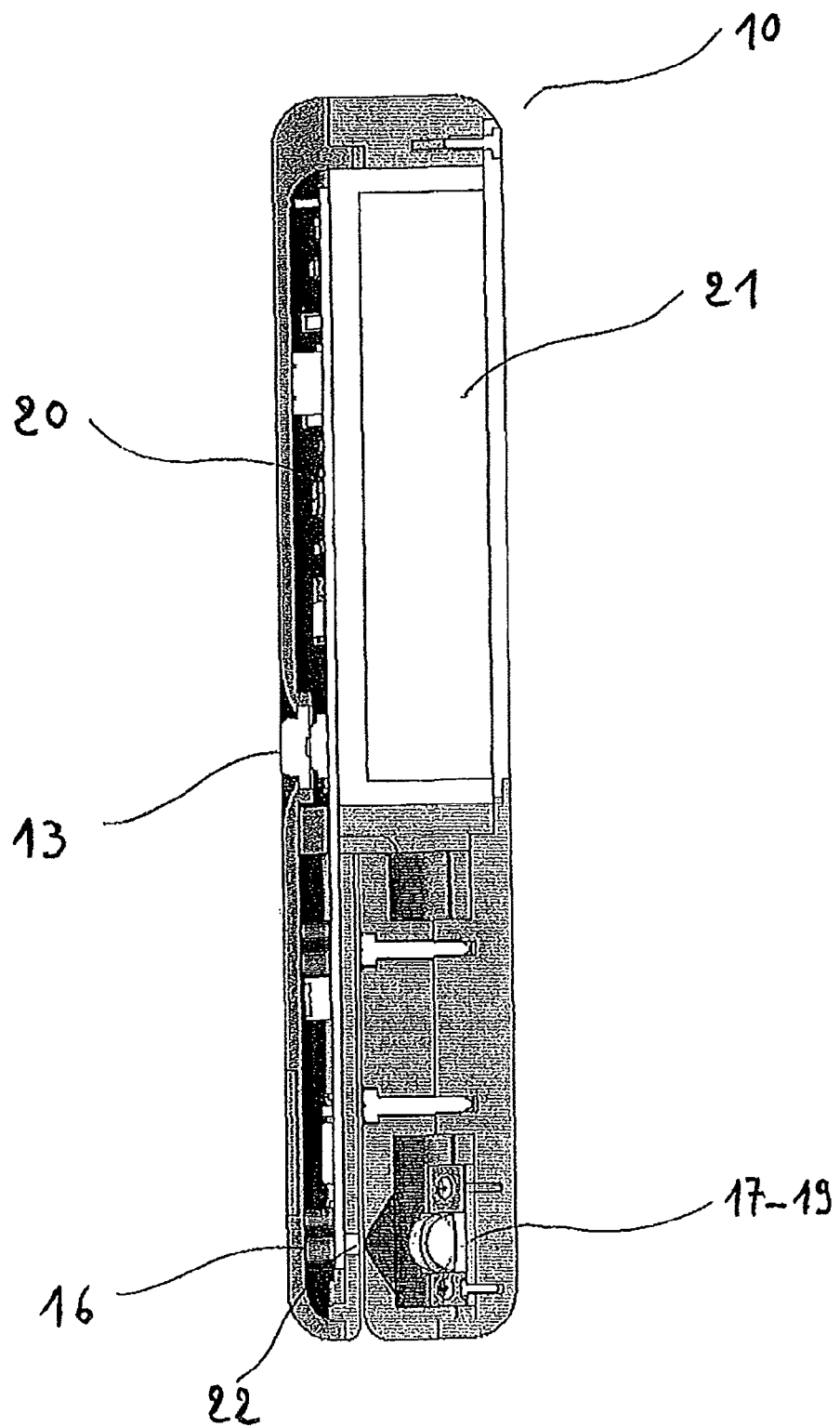
FIG. 3A-3B illustrate cut-away side views of the banknote validator of FIGS. 1-2.
Figure 3B:
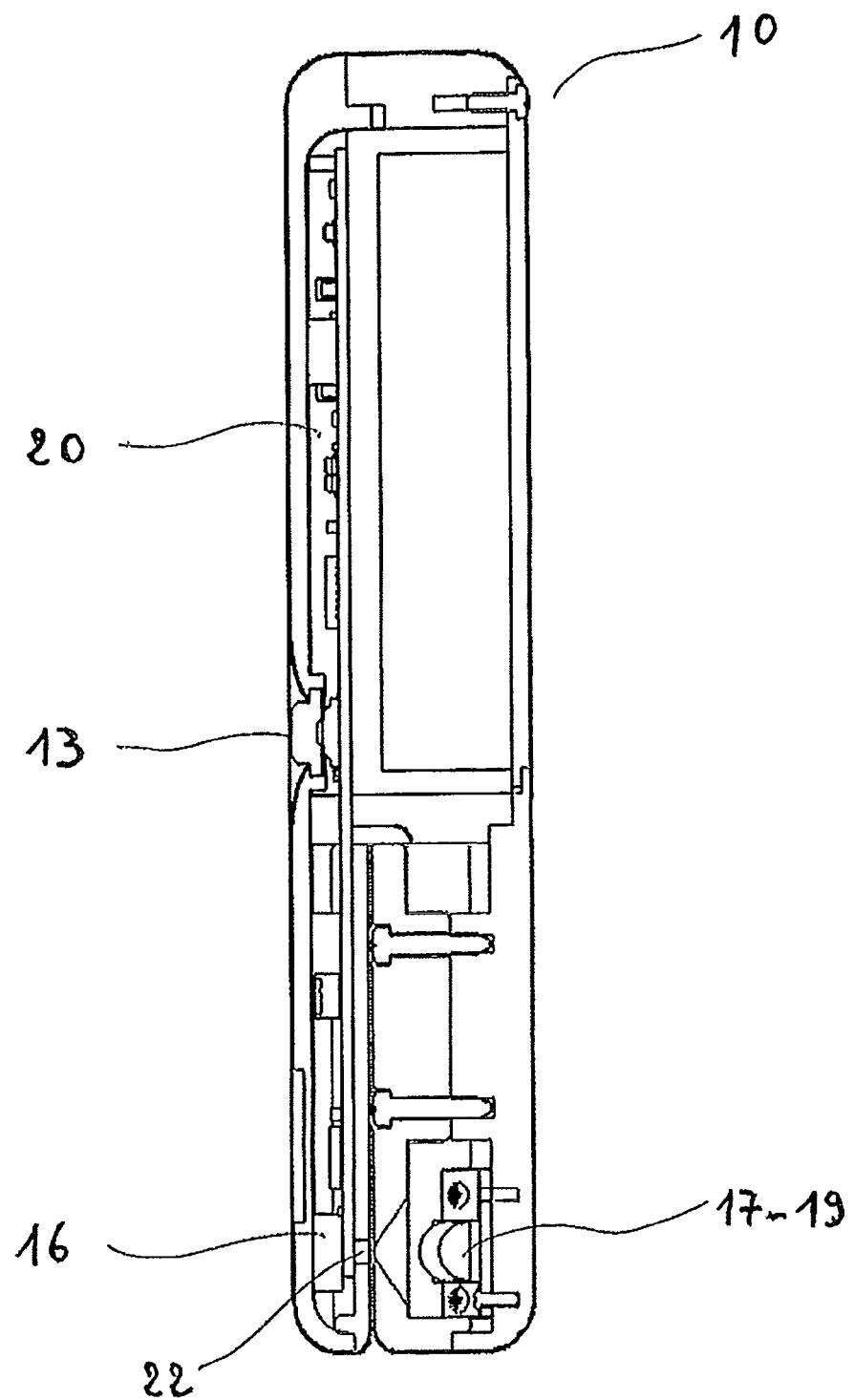
Figure 4A:
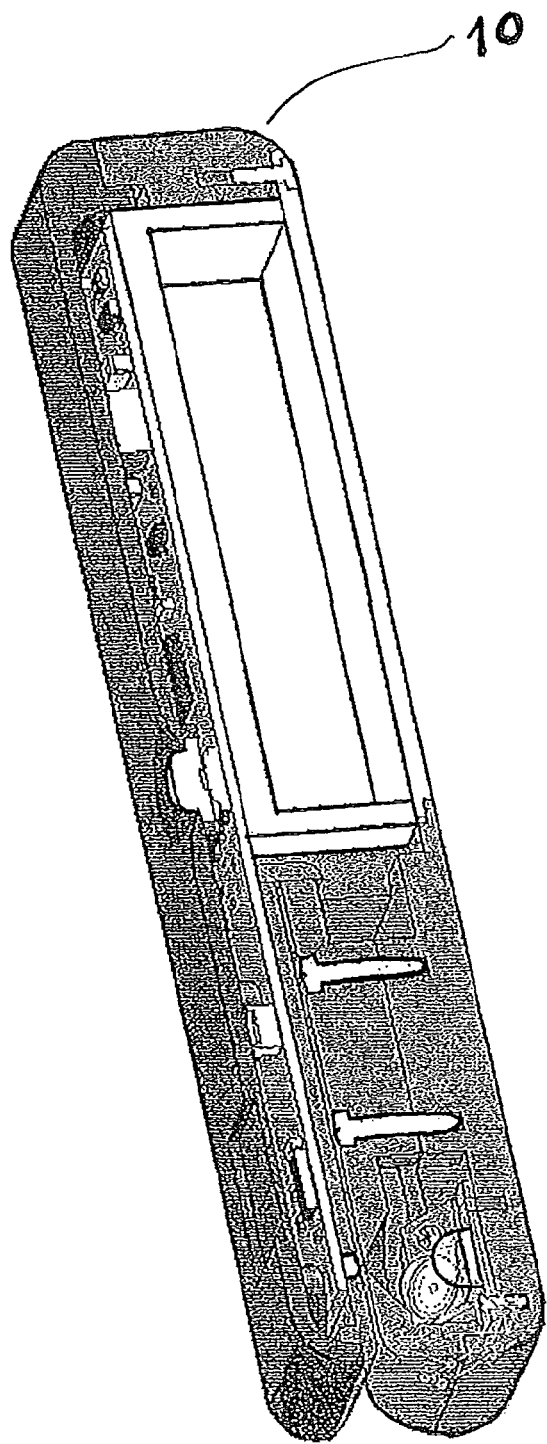
FIGS. 4A-4B illustrate cut-away perspective views of the banknote validator of FIG. 3.
Figure 4B:
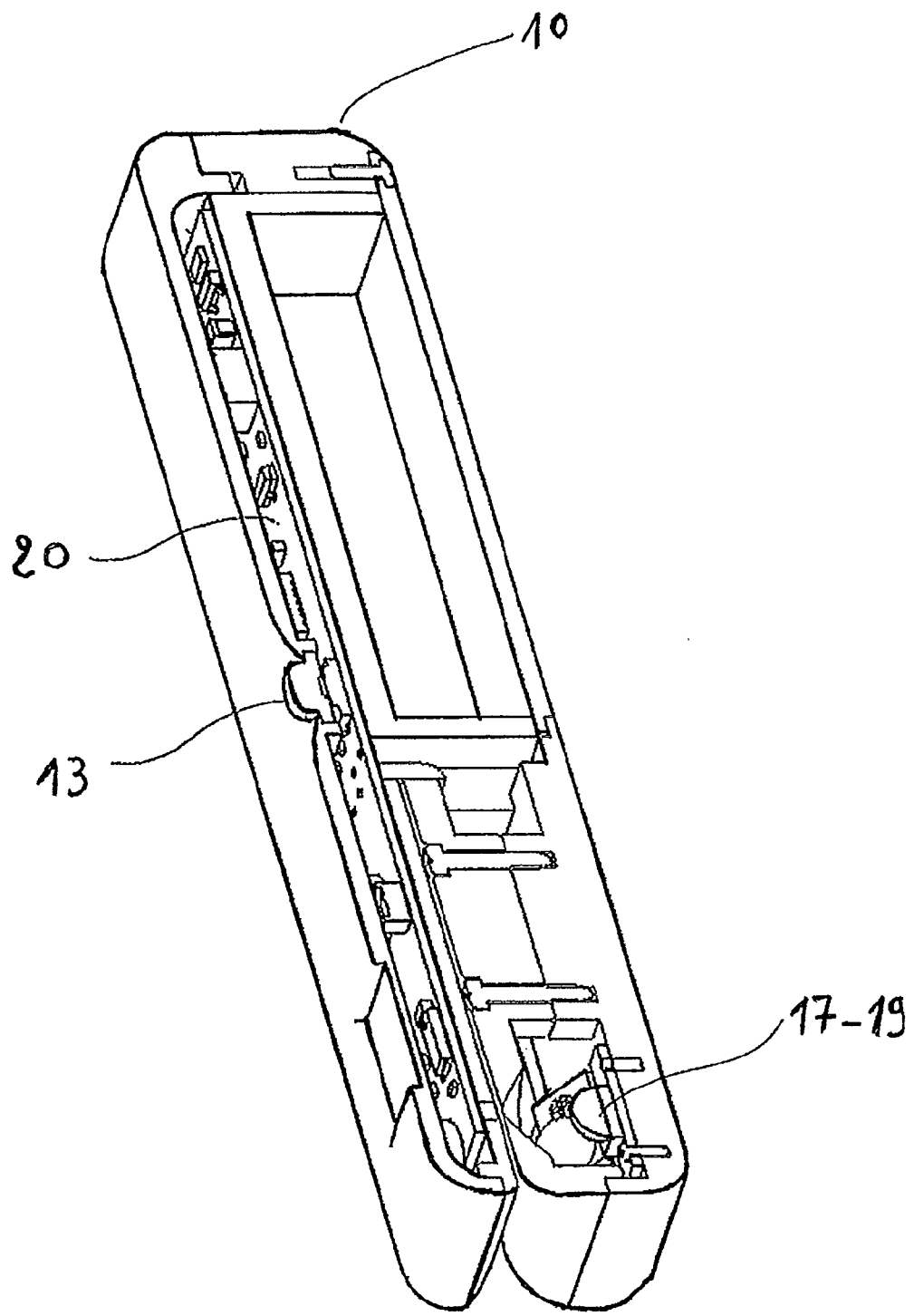

The banknote validator (10) represented in FIGS. 1, 2A and 2B, has a passageway (12) forming a U-shaped clip with an insertion slot which allows a user to easily both press the button (13) to switch power on, and insert and move a banknote (11) to be tested in and through said passageway (12). An upper branch (14) of the U-shaped clip contains a color sensor (22), which is here a RGB photodiode, and a lower branch (15) of the clip contains the light sources (17-19) for illuminating the banknote (11) having a security thread disposed along a width of said banknote (as it is the case for all denominations of the US currency).

As represented on FIGS. 3A, 3B, 4A and 4B, a control unit (20), including a CPU and a memory, is powered by a battery in a battery housing (21) and is connected to the switch (13), the color sensor (22) and the light sources (17-19). This control unit (20) controls and synchronizes the color sensor (22) and the light sources (17-19) so as to illuminate the banknote (11), detects a presence of corresponding light transmitted through the banknote to the color sensor (22), via an amplifier (16) in the upper branch (14) (which is connected to an A/D converter to send a digital signal to the CPU), and determines a color value, while the user presses the button (13) of the switch. An advantage of the color detection in transmission over reflection is that the measurement does not depend on orientation of the banknote.

In this example of an embodiment of the validator according to the invention, the light sources, as illustrated in greater detail in FIG. 5, comprise:

a first UV light source (17) which is a UV light emitting LED having a peak emission wavelength at 370 nm (±5 nm at 50%) (adapted to the US currency), and further equipped with a half-ball sapphire lens (17') for concentrating the emitted light toward the RGB photodiode (22);

a second UV light source (18) which is a UV light emitting LED having a peak emission wavelength at 390 nm (±5 nm at 50%) (adapted to the US currency), and further equipped with a half-ball sapphire lens (18') for concentrating the emitted light toward the RGB photodiode (22); and a third light source (19) which is a blue light emitting LED having a peak emission wavelength at 410 nm (±5 nm at 50%), and also further equipped with a half-ball sapphire lens (19') for concentrating the emitted light toward the RGB photodiode (22).

The RGB photodiode (22) (here a Si photodiode S10170 of Hamamatsu) is equipped with RGB color filters and is operable to detect red light for a peak wavelength of 720 nm (±112 nm at 50%), green light for a peak wavelength of 544 nm (±34 nm at 50%), and blue light for a peak wavelength of 468 nm (±40 nm at 50%).

The control unit (20) is operable to:

determine a first color value of the first excited luminescence light emitted by the security thread, from a first signal received from the color sensor (22) in response to illumination of the banknote (11) with the first light source (17);

determine a second color value of the second excited luminescence light emitted by the security thread, from a second signal received from the color sensor (22) in response to illumination of the banknote (11) with the second light source (18); and then compare said determined color values with stored distinct reference color values corresponding to distinct genuine denominations, and, in case the determined color values match reference color values, determine that the denomination of the banknote (11) corresponds to that associated with said reference color values; and control the communicator to indicate the determined denomination.

Said communicator (not represented) may be, for example, either:

visual: like LEDs of different colors (for different denominations), or a display, or non-visual: like vocal communication, or based on coded noise or vibration emission, or tactile (like Braille code), these non-visual communications being adapted to visually impaired users.

Moreover, the control unit (20) is further operable to control the first UV light source (17) and the second UV light source (18), and the color sensor (22), so as to:

illuminate the banknote (11) with either the first light source or the second light source, or with both light sources;

then interrupt the illumination of the banknote and measure a decay time value of the excited luminescence (phosphorescence) light from the security thread with the color sensor (22), over a given period of time (typically of about 1 to 10 ms), by performing successive measurements with the color sensor over said period of time;

compare the measured decay time value with distinct reference decay time values stored in the memory and corresponding to genuine distinct denominations; and in case the determined color values match reference color values, judge that the denomination of the banknote corresponds to that associated with said reference color values (as indicated above) only if the measured decay time value further matches a reference decay time value corresponding to said previously determined denomination (i.e. based on the matching of color values). Then, the control the communicator (20) indicates the determined denomination.

In fact, the first light source (17), or the second light source (18), allows detecting by the color sensor (22):

the security thread luminescence color;

a presence of an optical brightener agent in the paper, as it will reveal a dominant blue color emitted all along the banknote (instead of punctually in the case of the security thread);

a presence of highlighter pen inks, when considered together with the third light source (19) illumination, as such material will not only glow under the first light source (17) illumination but also under the third light source (19) illumination; and a luminous decay in the security thread of the $10 and $100 (new series).

The third light source (19) allows detecting by the color sensor (22) a luminescence excited by the emitted third light and coming from a highlighter pen ink, and verifying the non-luminescence of the security thread under said third light exposure.

Using the first (17) and the second (18) light sources further allows discriminating the old series $10 and $50. Indeed, under illumination only by the first source light (17), at 370 nm, the security thread of each one of the denomination $10 and $50 from old series fluoresces and glows with yellow color. Under illumination by the second source light (18), at 390 nm, the security thread of the $10 (old series) glows with orange color, while the security thread of the $50 (old series) still glows with yellow color.

Figure 6:
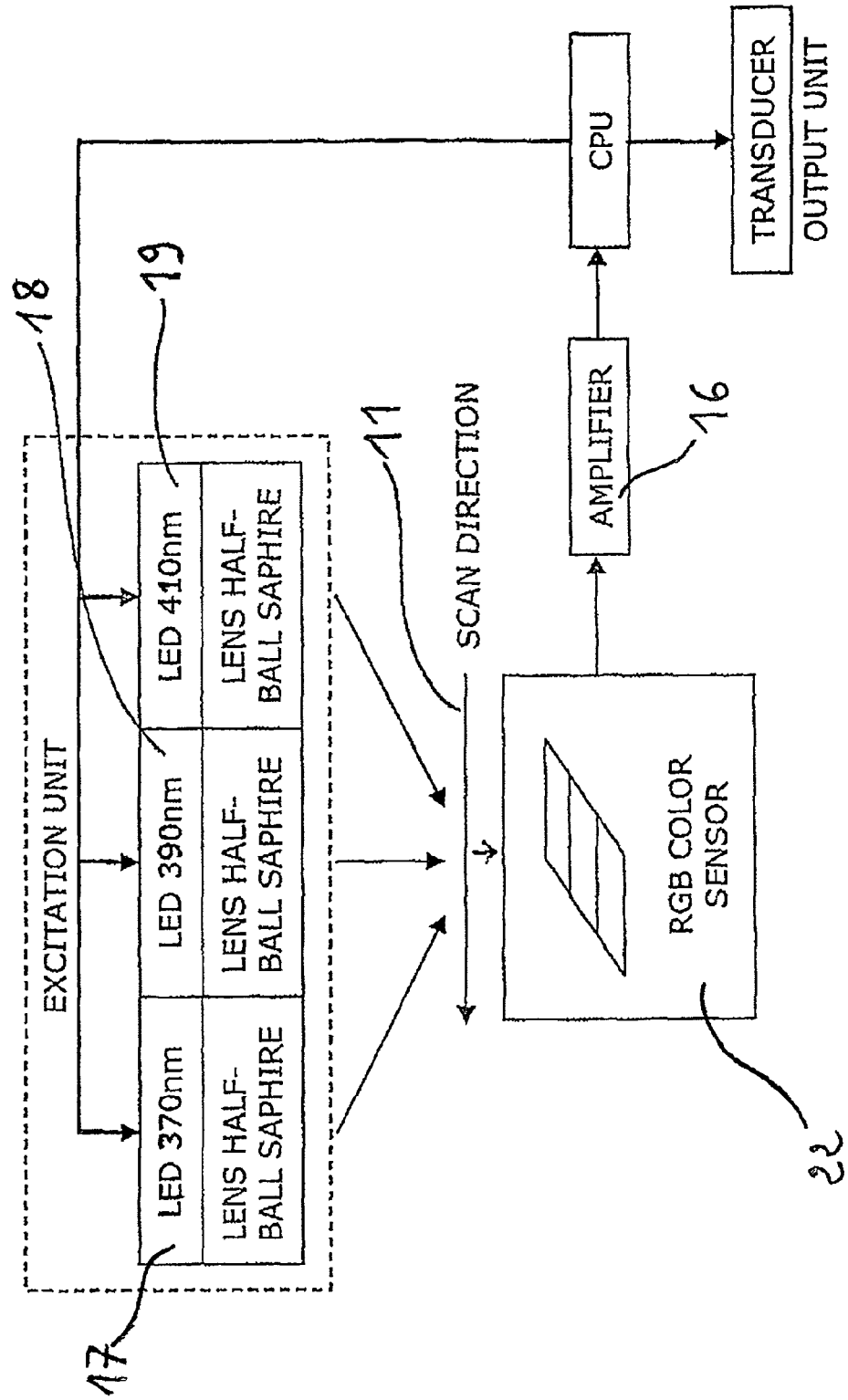
FIG. 6 is a schematic diagram of the banknote validator of FIGS. 1-5.

FIG. 6 is a schematic diagram illustrating the banknote validator (10). The user inserts the banknote (11) in the passageway (12) and slides banknote (11) forward through passageway (12), while pushing the button (13) to switch on the validator (in order to provide power for the illumination and detection). Then, the control unit (20) detects the presence of the banknote via the detection of an illumination threshold by the color sensor (22) through amplifier (16). The first light source (17) illuminates the banknote (11) moving in the passageway, and when the security thread passes in front of the color sensor (22) (which delimits a test zone for detection on the banknote), it glows under said illumination and the color sensor (22) determines a corresponding first color value from the first excited luminescence light transmitted through the banknote. The control unit (20) then compares the first color value to reference color values to check a matching. The second light source (18) is then switched on and further illuminates the banknote. The color sensor (22) then determines a corresponding second color value from the second excited luminescence light transmitted through the banknote and the control unit (20) compares the second color value to reference color values to check a matching. After a period of time sufficient to allow detecting a decay due to a phosphorescent emission from the security thread (typically, about 1 ms), the light sources (17) and (18) are switched off and illumination of the security thread is interrupted. Then, color sensor (22) detects a decay of the luminescence light received from the security thread. The control unit (20) determines the denomination of the banknote, or decides it is not valid, and controls the communicator (transducer 23) accordingly.

The third light source (19) may also be used for further testing that a luminescence color caused by the third light illumination of the security thread is not present (in case it is present, the banknote is not valid).

For example, with a $5 tested, there is no decay, and the color values match the blue reference value. For a $10 tested, a decay is detected (thus only the denominations $10 new series and $100 are candidate), and the first and second color values respectively match the orange reference value, then the $10 denomination for the tested banknote is validated. If for a $10 tested, a decay is not detected (thus the banknote cannot be a $10 new series or a $100), the first and second color values respectively match the orange reference value, then the tested banknote is not valid. By contrast, if the first and second color values respectively match the yellow and orange reference values, then the $10 denomination old series for the tested banknote is validated.

Figure 7:
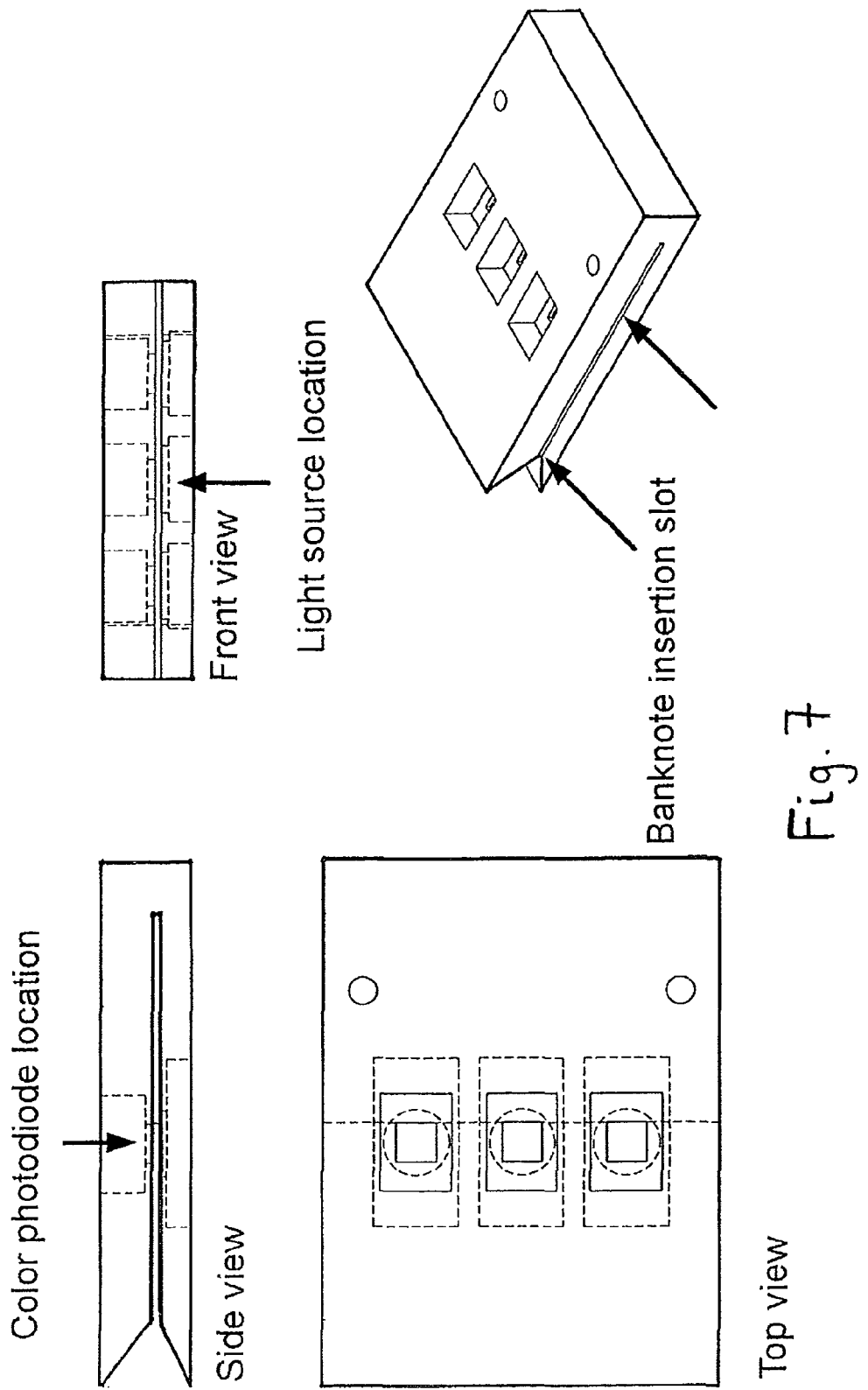
FIGS. 7(a)-7(d) illustrate an alternative embodiment of the handheld banknote validator according to the invention.

The invention is not limited to the above embodiments and various modifications may be made without departing from the scope of the invention as defined by the claims. For example, the shape of the validator and/or the disposition of the light sources and color sensors may be varied (as represented, for example, on FIG. 7). In contrast to the arrangement and configuration of the light sources (17-19) and color sensor (22) depicted in FIGS. 1-5, light sources (27-29) can be spaced apart along a length of passage (12') and individual color sensors (30-32) may be arranged to receive excited luminescence light resulting from illumination of a test zone by respective individual light sources (27-29). As with the embodiments of FIGS. 1-5, the first light source (27) can be arranged to emit light in a first wavelength range, the second light source (28) can be arranged to emit light in a second wavelength range, and the third light source (29) can be arranged to emit light in a third wavelength range. However, instead of the RGB color sensor (22) utilized in the embodiments of FIGS. 1-5, individual color sensors (30-32) can be positioned to receive respective corresponding first, second or third excited luminescence light transmitted through the test zone. Moreover, color sensors (30-32) can be arranged in the upper branch defining passage (12') and light sources (27-29) can be arranged in the lower branch. Further, it is understood that the color sensors and light sources can be arranged in the same branch in order to detect light reflection. Still further, in alternative embodiments, the passageway is not necessarily a clip. The peak values of the light sources, and those of the color sensors must be adapted, depending on the optical properties of the markings of the currency considered.

In a variant of the invention, only one UV light source is used and only one luminescence color is determined and compared with reference color values, and a decay time of phosphorescence light emitted by a marking in response to said UV light excitation is also measured: this combination suffices for discriminating the denominations of many currencies (other than the US one). Also, a further light source having a substantially blue light component (for example, a white source) may be added for detecting a highlighter pen ink. Color profiles may as well be established in this variant for identifying denominations.

The invention claimed is:

1. A banknote validator for identifying a denomination of a banknote having a test zone including a marking operable to glow with a specific color luminescence according to the denomination under appropriate ultraviolet (UV) light illumination, the banknote validator comprising:
a housing provided with a banknote passageway;
a first UV light source structured and arranged to irradiate in the passageway the test zone of the banknote with UV light in a first wavelength range to create a first excited luminescence light at least one of transmitted through and reflected from the test zone;
a first color sensor structured and arranged to receive the first excited luminescence light and to allow determining both a mean wavelength and an amplitude of a detected first excited luminescence light;
a second UV light source structured and arranged to irradiate the test zone of the banknote with UV light in a second wavelength range, distinct from the first wavelength range, to create a second excited luminescence light at least one of transmitted through and reflected from the test zone;
a second color sensor structured and arranged to receive corresponding second excited luminescence light and to allow determining both a mean wavelength and an amplitude of a detected second excited luminescence light;
a communicator structured and arranged indicate a denomination of the banknote; and
a processor configured to control the first and second UV ht sources the first and second color sensors and the communicator, the processor comprising a memory,
wherein the processor is further configured to:
determine a first color value of the first excited luminescence light from a first signal received from the first color sensor;
determine a second color value of the second excited luminescence light from a second signal received from the second color sensor;
compare the first and second color values with respective stored reference color values associated with luminescence under UV light in one of the first and second wavelength ranges;
determine a denomination of the banknote from reference color values corresponding to the first and second color values; and
control the communicator to indicate the determined denomination,
wherein the processor is further configured to:
control one of the first UV light source and the first color sensor or the second UV light source and the second color sensor so as to illuminate the banknote, interrupt the illumination of the banknote and detect a decay of a corresponding excited luminescence light; and
control the communicator to indicate the denomination only when the detected decay corresponds with the denomination.

2. A banknote validator for identifying a denomination of a banknote having a test zone including a marking operable to glow with a specific color luminescence according to the denomination under appropriate ultraviolet (UV) light illumination, the banknote validator comprising:
a housing provided with a banknote passageway;
a first UV light source structured and arranged to irradiate in the passageway the test zone of the banknote with UV light in a first wavelength range to create a first excited luminescence light at least one of transmitted through and reflected from the test zone;
a first color sensor structured and arranged to receive the first excited luminescence light and to allow determining both a mean wavelength and an amplitude of a detected first excited luminescence light;
a second UV light source structured and arranged to irradiate the test zone of the banknote with UV light in a second wavelength range, distinct from the first wavelength range, to create a second excited luminescence light at least one of transmitted through and reflected from the test zone;

a second color sensor structured and arranged to receive corresponding second excited luminescence light and to allow determining both a mean wavelength and an amplitude of a detected second excited luminescence light;

a communicator structured and arranged indicate a denomination of the banknote; and a processor configured to control the first and second UV light sources, the first and second color sensors and the communicator, the processor comprising a memory, wherein the processor is further configured to:

determine a first color value of the first excited luminescence light from a first signal received from the first color sensor;

determine a second color value of the second excited luminescence light from a second signal received from the second color sensor;

compare the first and second color values with respective stored reference color values associated with luminescence under UV light in one of the first and second wavelength ranges;

determine a denomination of the banknote from reference color values corresponding to the first and second color values; and control the communicator to indicate the determined denomination, wherein the processor is further configured to:

control one of the first UV light source and the first color sensor or the second UV light source and the second color sensor to illuminate the banknote, interrupt the illumination of the banknote and measure a decay time value of the excited luminescence light;

compare the measured decay time value with stored distinct reference decay time values corresponding to distinct denominations; and when the determined color values match reference color values for a particular denomination, determine that the measured decay time value matches a reference decay time value corresponding to the particular denomination.

3. A method for identifying a denomination of a banknote having a test zone including a marking operable to glow with a specific color luminescence according to the denomination under appropriate ultraviolet (UV) light illumination, the method comprising:

irradiating the test zone of the banknote with UV light in a first wavelength range to generate a first excited luminescence light at least one of transmitted through and reflected by the test zone;

determining a first color value of a received first excited luminescence light that corresponds to both a mean wavelength and amplitude of the first excited luminescence light;

irradiating the test zone of the banknote with UV light in a second wavelength range to generate a second excited luminescence light at least one of transmitted through and reflected from the test zone;

determining a second color value of the second excited luminescence light that corresponds to both a mean wavelength and amplitude of the second excited luminescence light;

comparing the determined color values with respective distinct reference color values for luminescence under UV light in the first and second wavelength ranges, respectively;

determining a denomination of the banknote based upon reference color values corresponding to the first and second color values;

communicating the determined denomination;

controlling at least one of the first UV light source and the first color sensor, or the second UV light source and the second color sensor to illuminate the banknote, to interrupt the illumination of the banknote and to detect a decay of a corresponding excited luminescence light; and communicating the denomination only when the detected decay corresponds with a decay associated with the denomination.

4. A method for identifying a denomination of a banknote having a test zone including a marking operable to glow with a specific color luminescence according to the denomination under appropriate ultraviolet (UV) light illumination, the method comprising:

irradiating the test zone of the banknote with UV light in a first wavelength range to generate a first excited luminescence light at least one of transmitted through and reflected by the test zone;

determining a first color value of a received first excited luminescence light that corresponds to both a mean wavelength and amplitude of the first excited luminescence light;

irradiating the test zone of the banknote with UV light in a second wavelength range to generate a second excited luminescence light at least one of transmitted through and reflected from the test zone;

determining a second color value of the second excited luminescence light that corresponds to both a mean wavelength and amplitude of the second excited luminescence light;

comparing the determined color values with respective distinct reference color values for luminescence under UV light in the first and second wavelength ranges, respectively;

determining a denomination of the banknote based upon reference color values corresponding to the first and second color values;

communicating the determined denomination;

controlling at least one of the first UV light source and the first color sensor or the second UV light source and the second color sensor to illuminate the banknote, to interrupt the illumination of the banknote and to measure a decay time value of the excited luminescence light;

comparing the measured decay time value with stored distinct reference decay time values corresponding to distinct denominations; and when the determined color values match reference color values, determining that the denomination of the banknote corresponds to a denomination value associated with the reference color values when the measured decay time value matches a reference decay time value corresponding to the denomination value.

* * * * *

UNITED STATES PATENT AND TRADEMARK OFFICE
CERTIFICATE OF CORRECTION

| | | |
|---|---|---|
| PATENT NO. | : 9,240,086 B2 | Page 1 of 1 |
| APPLICATION NO. | : 13/504790 | |
| DATED | : January 19, 2016 | |
| INVENTOR(S) | : E. Decoux | |

It is certified that error appears in the above-identified patent and that said Letters Patent is hereby corrected as shown below:

In the claims,

Column 14, line 21 (claim 1, line 29) please change "UV ht" to -- UV light --

Column 14, line 22 (claim 1, line 30) please change "sources the" to -- sources, the --

Signed and Sealed this
Twenty-third Day of August, 2016

Michelle K. Lee
*Director of the United States Patent and Trademark Office*